(12) United States Patent
Shiohama

(10) Patent No.: US 9,285,381 B2
(45) Date of Patent: Mar. 15, 2016

(54) ANALYZING APPARATUS CONTROL SYSTEM AND PROGRAM FOR CHROMATOGRAPH MEASUREMENTS

(75) Inventor: Tohru Shiohama, Osaka (JP)

(73) Assignee: SHIMADZU CORPORATION, Kyoto (JP)

(*) Notice: Subject to any disclaimer, the term of this patent is extended or adjusted under 35 U.S.C. 154(b) by 175 days.

(21) Appl. No.: 13/552,474

(22) Filed: Jul. 18, 2012

(65) Prior Publication Data

US 2014/0022254 A1    Jan. 23, 2014

(51) Int. Cl.
G06T 11/20 (2006.01)
G01N 30/72 (2006.01)
G01N 35/00 (2006.01)
G01N 30/86 (2006.01)

(52) U.S. Cl.
CPC ........ *G01N 35/0092* (2013.01); *G01N 30/8644* (2013.01)

(58) Field of Classification Search
CPC ..... A23V 2002/00; G01N 30/72; G06T 11/20
USPC ......................................................... 345/440
See application file for complete search history.

(56) References Cited

U.S. PATENT DOCUMENTS

| 8,168,942 | B2 | 5/2012 | Sumiyoshi | |
| 2003/0131286 | A1* | 7/2003 | Kaler et al. | 714/39 |
| 2009/0008542 | A1* | 1/2009 | Sumiyoshi | 250/281 |

FOREIGN PATENT DOCUMENTS

| JP | 04294271 A | 10/1992 |
| JP | 2005-083952 | 3/2005 |
| JP | 2011-058982 | 3/2011 |
| WO | 2007102201 A1 | 9/2007 |

OTHER PUBLICATIONS

Japanese Office Action mailed Dec. 3, 2013 for corresponding Japanese Patent App. No. 2010-002630.
Japanese language office action dated Apr. 9, 2013 and its English language translation issued in corresponding Japanese application 2010002630 cites the foreign patent documents listed above.

* cited by examiner

*Primary Examiner* — Ming Hon
*Assistant Examiner* — Shivang Patel
(74) *Attorney, Agent, or Firm* — Morgan, Lewis & Bockius LLP

(57) ABSTRACT

In an analyzing apparatus which is connected to a chromatograph, in which one more measurement events are performed based on a reference chromatogram, when multiple events overlap each other and are simultaneously performed, a loop time may become too long and therefore the measurement may not be properly performed. The system of the present invention includes: a time range displayer for displaying each of one or more measurement time ranges as a range bar; and a loop time displayer for computing a loop time, which is a time required for a unit measurement, for each of the measurement time ranges and displaying results of computations. Thereby, a user can intuitively know whether or not the measurement requires an adjustment.

9 Claims, 5 Drawing Sheets

Prior Art

ANALYZING APPARATUS CONTROL SYSTEM AND PROGRAM FOR CHROMATOGRAPH MEASUREMENTS

TECHNICAL FIELD

The present invention relates to a system for controlling an analyzing apparatus and a program for this system. In particular, the present invention relates to a system and a program for setting conditions of an analysis in an analyzing apparatus which includes a chromatograph or is connected to a chromatograph.

BACKGROUND ART

In a chromatograph mass spectrometer, in which a chromatograph and a mass analyzer are combined, a sample is temporally separated by the chromatograph in the first stage, and then the separated sample is mass-analyzed in the mass analyzer in the subsequent stage (refer to Patent Document 1, for example).

In the mass analyzer of the subsequent stage, a measurement is usually not performed on the entire sample that has been temporally separated and introduced into the mass analyzer. Instead, a predetermined measurement is performed only on each area of fluctuation in the chromatogram, e.g. where a peak or peaks exist. That is, the measurement is performed only on one or more time ranges.

Therefore, a time range setting operation is required to perform an intended analysis. To do so, it is necessary to prepare a chromatograph of the same sample in advance for use as a reference by the user to set which measurement is performed at which point in time.

A control application for controlling an analyzing apparatus is used to set the time ranges. Conventionally, a user enters numbers to represent the time in predetermined entry fields while referring to a reference chromatograph. An example of the screen of such a conventional analyzing apparatus control application is shown in FIG. 8. In the left column of the screen in this example screen, the chromatograph measurement time ranges are divided into the following segments: "segment 1"=[0.000-10.000] (minutes) and "segment 2"=[10.000-20.000] (minutes). Measurements "event 1" and "event 2" in "segment 1", and measurement "event 1" in "segment 2" have been entered manually.

Hereinafter, a measurement carried out under predetermined conditions from among multiple measurements performed within a certain period of time will be called an "event."

In a conventional chromatograph mass spectrometer, the time range for a measurement with certain conditions requires manual designation when setting the conditions of measurement for a mass analyzer, so the operation tends to be complicated, and it can cause input errors. Given this, the inventor of the present invention has already made an invention with the aim of providing an analyzing system control system which allows users to set the conditions of analysis more intuitively and simply than ever before. This invention has been filed prior to the present application and published as JP-A 2011-058982. This system provides a graphical user interface as shown in FIG. 9 and achieves such things as the effects below.

The time ranges of measurements are shown as range bars which are temporally superimposed on a reference chromatograph in a display unit (or monitor). This enables a user to immediately understand the relationship between the reference chromatogram and the measurements to be performed. Additionally, the relationships between multiple measurements that are performed on one sample are immediately visually recognized. Consequently, the burden of setting the conditions of measurements is alleviated and mistakes in the setting operation can be prevented.

The time range when the measurement will be performed can be altered by the user simply operating an input unit such as a mouse to adjust the length of a range bar or change its temporal position shown on the display unit. This enables a flexible setting of time ranges, facilitates operation, and also ensures a reduction of mistakes in the setting operation compared to the case where time ranges are set manually.

BACKGROUND ART DOCUMENT

Patent Document

[Patent Document 1] JP-A 2005-083952

DISCLOSURE OF THE INVENTION

Problem to be Solved by the Invention

Generally, in an analyzing apparatus such as a chromatograph mass spectrometer, multiple measurements are repeated in an event set in a specified time range (ten times or more, in general) with the aim of reducing noise and other purposes. If the number of events performed simultaneously is one (i.e. only one event exists at a time point or time range), the second measurement for the event is started just after the first measurement of the event ends, for example. If the number of events performed simultaneously is more than one (i.e. two or more events exist at a time point or time points), the next series of measurements are started after a series of measurements for all of the events ends. That is, when the number of events is more than one, "one measurement" means the completion of a series of measurements of all the events.

Hereinafter, one measurement of one or more events set on a specified time range will be called a "unit measurement," and the time required for a unit measurement will be called a "loop time."

The loop time is the total of "summation of the measurement times of all events" and the "time required for other operations such as changing the detector." Hence, the loop time will be long if multiple events overlap each other and are performed simultaneously. A resulting problem is that the loop time may exceed an allotted time for the unit measurement in some cases, so that measurement cannot be performed accurately, the reliability of the measurement results decreases, or even the measurement itself fails to be performed.

Given those factors, adjustments are required when setting the conditions of measurements so as to decrease the number of overlapping events in order to prevent the loop time from becoming excessively long. Conventionally, however, the user himself/herself has to carry out a computation to calculate the loop time, which requires a very cumbersome operation.

The present invention has been developed to solve the aforementioned problem.

Means for Solving the Problem

To solve the aforementioned problem, the present invention provides an analyzing apparatus control system for controlling an analyzing apparatus so as to temporally separate a sample to be examined by a chromatograph, and repeat unit measurements in each of one or more measurement time ranges set in a total measurement time, including:

a) a time range displayer for displaying each of the one or more measurement time ranges as a range bar; and b) a loop time displayer for computing a loop time, which is a time required for a unit measurement, for each of the measurement time ranges and displaying results of the computations.

Preferably, the analyzing apparatus control system according to the present invention may further include a chromatogram displayer for displaying a reference chromatogram which corresponds to the sample to be examined, and the time range displayer may display the range bars so as to temporally overlap the reference chromatogram which is displayed by the chromatogram displayer.

Here, "temporally overlapping" means that the chromatograph and the range bars actually overlap each other on the screen, or that they overlap each other in their corresponding time range in the direction of the time axis, despite the chromatograph and the range bars being separated in the direction of the intensity axis.

The present invention also provides an analyzing apparatus control program for controlling an analyzing apparatus so as to temporally separate a sample to be examined by a chromatograph, and repeat unit measurements in each of one or more measurement time ranges set in a total measurement time, the program being for making a computer which executes the program function as:

a) a time range displayer for displaying each of the one or more measurement time ranges as a range bar; and b) a loop time displayer for computing a loop time, which is a time required for a unit measurement, for each of the measurement time ranges and displaying the results of the computations.

The apparatus which is controlled by the analyzing apparatus control system according to the present invention can be any type of apparatus that analyzes and measures a sample that has been temporally separated by a chromatograph, such as a liquid chromatograph mass spectrometer.

Effects of the Invention

In the analyzing apparatus control system according to the present invention, the loop time of each measurement time range is computed and shown in the settings screen for the measurement conditions of a sample to be measured which will be separated by the chromatograph. This allows a user to check the computational results and know whether or not the values of the loop times are proper, and if a modification is necessary, the user can reconfigure the conditions of the measurement of the sample and other parameters so as to adjust the overlaps of the multiple events.

BEST MODE FOR CARRYING OUT THE INVENTION

Hereinafter, an example of the embodiment of the analyzing apparatus control system according to the present invention will be described in detail with reference to the figures.

Figure 1:
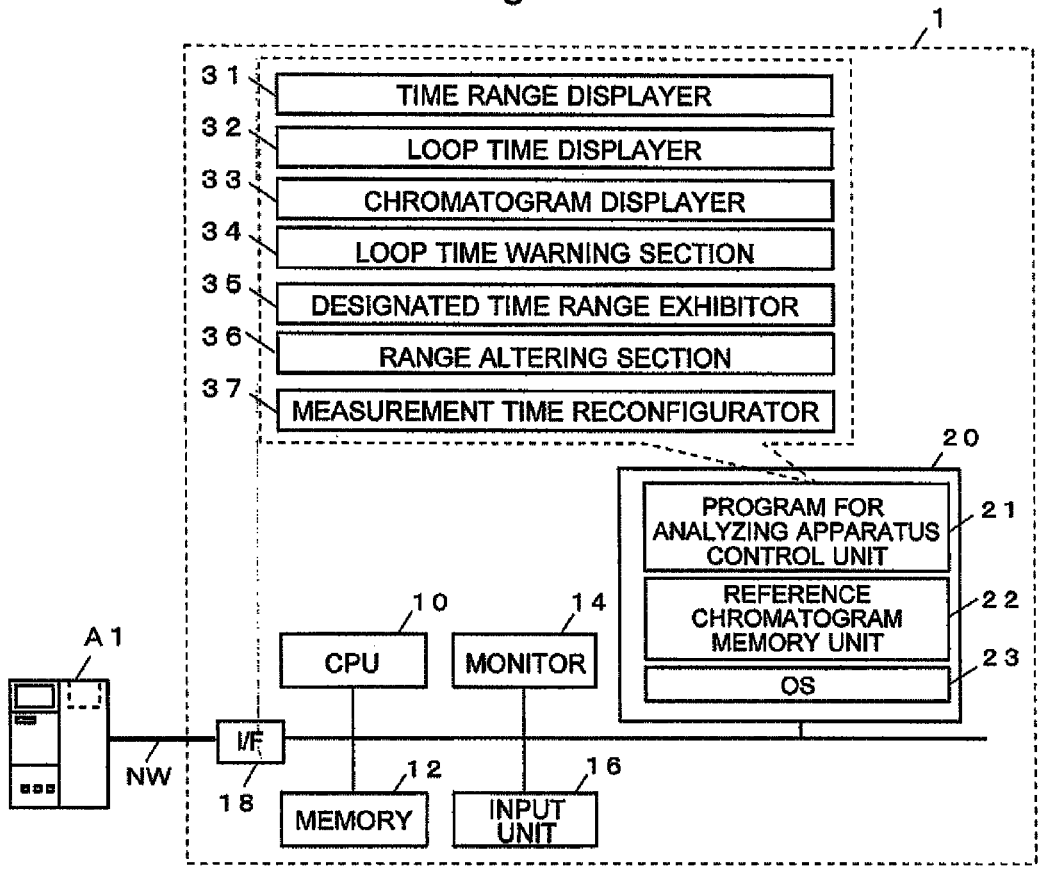
FIG. 1 is a schematic configuration of an embodiment of the analyzing apparatus control system according to the present invention.

FIG. 1 shows an embodiment of the analyzing apparatus control system 1 according to the present invention. The analyzing apparatus control system 1 is implemented by a computer, in which a memory 12, a monitor (display unit) 14 such as a liquid crystal display (LCD) 14, an input unit 16 such as a keyboard and a mouse, and a memory unit 20 such as a mass storage device, which is typically a hard disk drive or a solid state drive (SSD), are all connected to a central processing unit (CPU). A program 21 for an analyzing apparatus control system and a reference chromatogram memory unit 22 are stored in the memory unit 20. In the memory unit 20, an operating system (OS) 23 is also stored.

The analyzing apparatus control system 1 according to the present embodiment has an interface (I/F) 18 for controlling a direct connection with an external device or a connection through a network such as a Local Area Network (LAN). The analyzing apparatus control system 1 is connected with an analyzing apparatus A1, which is a chromatograph mass spectrometer. The analyzing apparatus control system according to the present invention does not necessarily have to be connected with an externally provided analyzing apparatus through the I/F 18, but may be integrated with an analyzing apparatus.

In the analyzing apparatus control system 1 according to the present embodiment, the OS 23 and the program 21 for an analyzing apparatus control system are provided separately. Of course, the program 21 for an analyzing apparatus control system may be integrated in a pan of the OS 23.

FIG. 1 shows a time range displayer 31, a loop time displayer 32, a chromatogram displayer 33, a loop time warning section 34, a designated time range exhibitor 35, a range altering section 36, and a measurement time reconfigurator 37. They are basically implemented as software components when the CPU 10 executes the program 21 for an analyzing apparatus control system.

Figure 2:
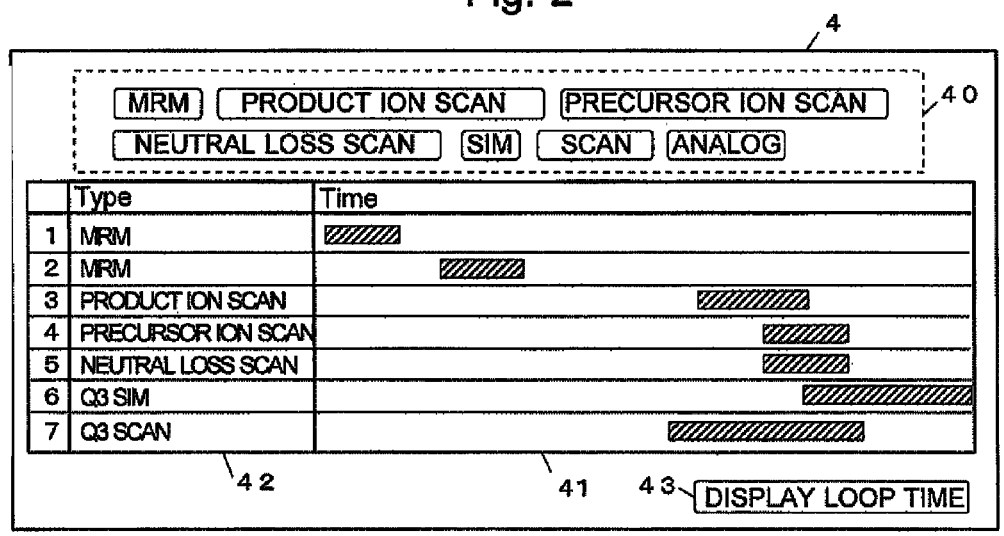
FIG. 2 shows an example of a measurement condition setting screen.

Next, the operation of the analyzing apparatus control system 1 according to the present embodiment will be described. First, a user instructs an execution of the program 21 for an analyzing apparatus control system by appropriate operation of the input unit 16 (e.g. double-clicks an icon displayed on the monitor 14) in order to display a screen on the monitor 14 for setting the measurement conditions for a mass analyzer which composes the analyzing apparatus A1. FIG. 2 shows an example of a measurement condition setting screen 4 as just described. The measurement condition setting screen 4 includes a measurement addition button area 40, a measurement time range display area 41, a measurement condition name display area 42, and other components.

The operations of the time range displayer 31, the loop time displayer 32, the chromatogram displayer 33, the loop time warning section 34, the designated time range exhibitor 35, the range altering section 36, and the measurement time reconfigurator 37 will now be described.

The user inputs measurements to be performed on the measurement condition setting screen 4 (e.g. presses a button placed in the measurement addition button area 40) so that each time the input operation is performed, the time range displayer 31 displays a range bar which visualizes the time range of each measurement in the measurement time range display area 41 in order for the range bars not to overlap each other. In the example of FIG. 2, a total of seven measurements have been set with measurement numbers 1 through 7, and the time ranges in which these measurements will be performed are displayed as range bars in the measurement time range display area 41. At this point in time, the user also completes the advanced settings for parameters for each measurement and other information. For example, detailed conditions for a measurement, as well as a measurement condition setting area for allowing the user to change the measurement conditions are displayed (not shown) on part of the measurement condition setting screen 4. The user can make detailed settings in that area.

Figures 3, 4:
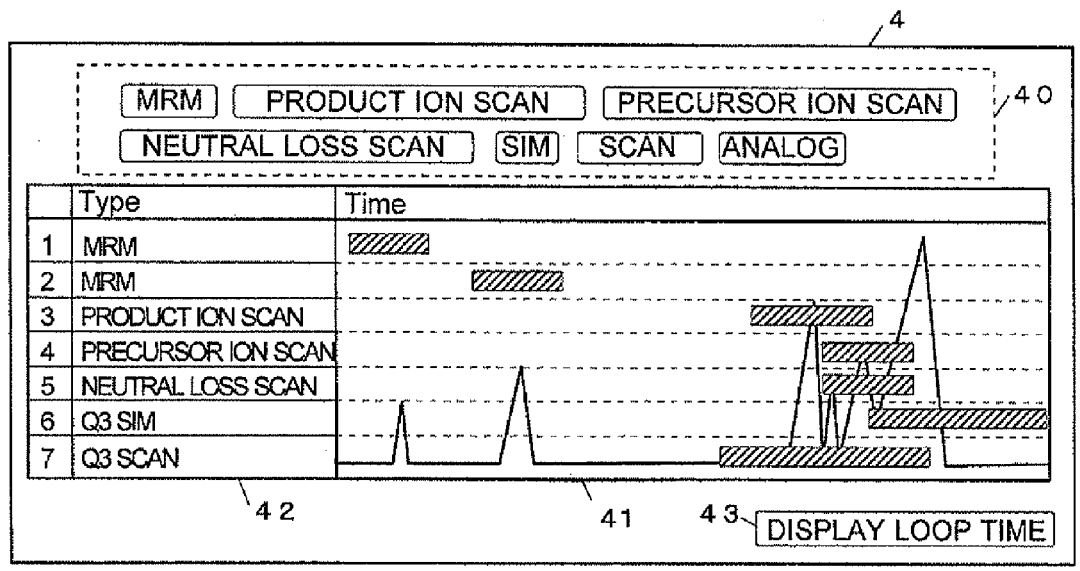
FIG. 3 shows another example of a measurement condition setting screen.
FIG. 4 shows an example of a loop time computational result window.

When setting events (i.e. measurements) on the measurement condition setting screen 4, a sample to be measured is set based on an instruction by the user or in some other manner, and the chromatogram displayer 33 reads out the data of a reference chromatogram that is appropriate to the sample from among the reference chromatograms which have been stored in advance in the reference chromatogram memory unit 22. The data is then displayed in the measurement time range display area 41 in the measurement condition setting screen 4 (FIG. 3). Of course, the user may directly select a desired reference chromatogram.

In this process, the entire reference chromatogram may be preferably displayed in the measurement time range display area 41. However, only a portion of the reference chromatogram may be displayed in the measurement time range display area 41, if the reference chromatogram is horizontally (i.e. in the time direction) long, or when a part of the reference chromatogram is enlarged. In this case, the chromatogram displayer 33 responds to a user instruction to scroll (i.e. when a button for instructing a scroll to the right is pressed), by changing the display position of the reference chromatogram in the measurement time range display area 41.

When the user correctly operates the input unit 16 to press the "display loop time" button 43 in the measurement condition setting screen 4 shown in FIG. 2 or 3, the loop time displayer 32 computes the loop time (the time required for a unit measurement) for each measurement, and displays the computational results in a predetermined area (e.g. on the measurement condition setting screen) on the monitor 14. FIG. 4 shows an example of the loop time computational result window 5 for displaying the computational results table.

In the loop time computational result window 5 shown in FIG. 4, loop times are listed as a result of the process by the loop time displayer 32. The table shows that the stall-finish times (measurement time ranges) of the loop time change from 5, -(none), 15, -, 25, 60, 140, 160, to 45 (sec). The loop time computational result window 5 shows the number of overlapping events in each measurement time range as a result of the operation of the loop time displayer 32.

In addition, a result of pressing the "display loop time" button 43 is that the loop time warning section 34 first compares each loop time computed by the loop time displayer 32 with a predetermined value. This "predetermined value" may be an actual value which has been set in advance, or a value determined by the length of the time range which has been set for the measurement (e.g. the time range length itself). If the result of this comparison is that the value of a loop time exceeds the predetermined value, the loop time warning section 34 displays a warning in the loop time computational result window 5. In the example of FIG. 4, the display areas with the loop times of 140 and 160 sec are highlighted in a different color, such as red. In this manner, sections with seemingly inappropriate loop times are visually reported to the user.

Figure 5:
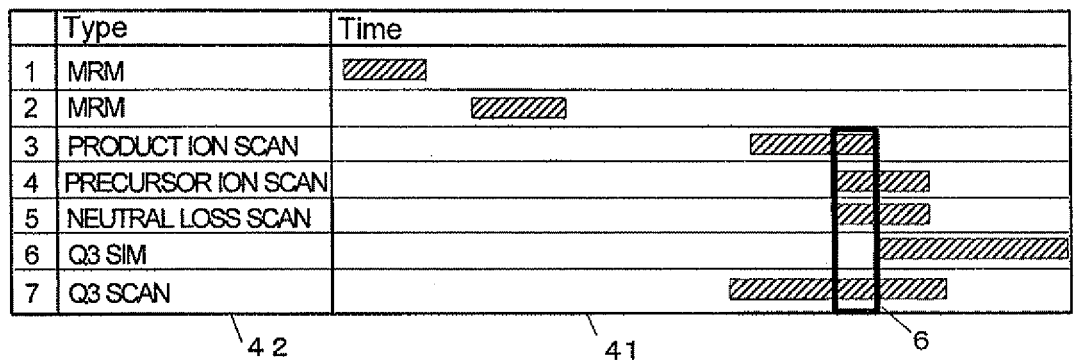
FIG. 5 is a schematic diagram showing an example of the operation of the designated time range exhibitor.

When the user correctly operates the input unit 16 to designate the time range of a loop time on the loop time computational result window 5 (e.g. the user operates the mouse pointer 51 and clicks on any one of the loop times, the start-finish time, and the number of events), the designated time range exhibitor 35 superposes the designated time range onto the range bars which are shown in the measurement time range display area 41. In the example shown in FIG. 5, as the time range of the loop time has been set at "140", the measurements of the measurement numbers 3 through 7 are partially enclosed in a thick-frame. This enables the user to visually understand the relationship between the loop times shown in the loop time computational result window 5 and the measurement time range display area 41.

Figure 6:
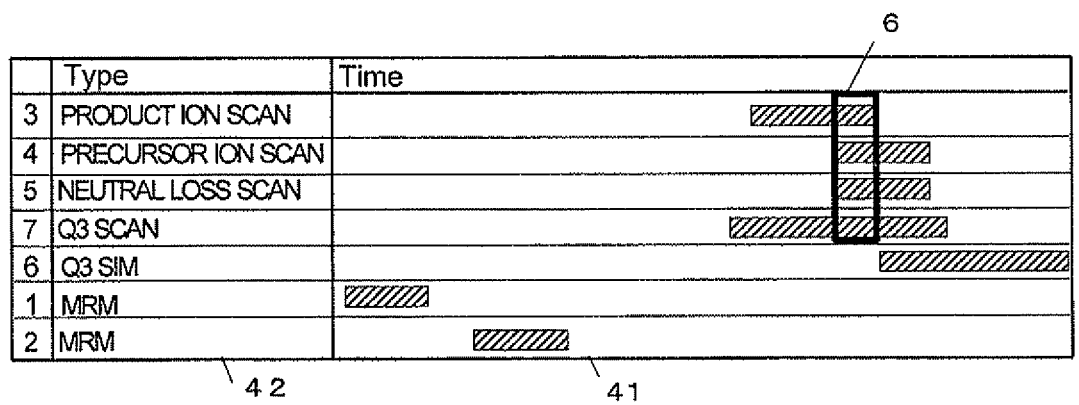
FIG. 6 is a schematic diagram showing another example of the operation of the designated time range exhibitor.

As shown in FIG. 6, the order of the range bars may be changed by the designated time range exhibitor 35 so that the multiple range bars in the designated loop time are situated adjacently. In the example of FIG. 6, the range bars (as well as the measurement names described in the measurement condition name display area 42) corresponding to the events with event numbers 3, 4, 5, and 7, which are included in the time range of the loop time "140," are reordered so as to be adjacent to each other. This enables the user to easily understand which measurements temporally overlap one another, especially when there are many events.

Figures 7, 8:
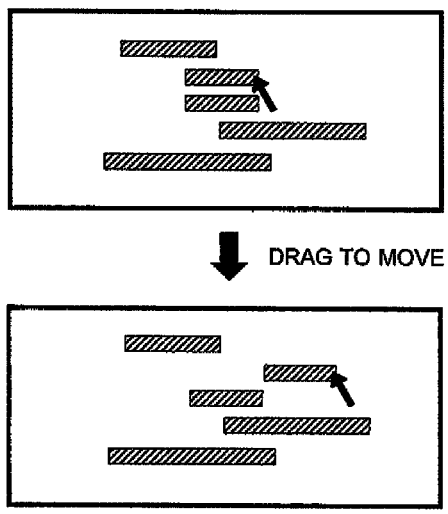
FIG. 7 is a diagram showing a schematic example of the operation of the range altering section.
FIG. 8 shows an example of a screen of a conventional analyzing apparatus control application.
Figure 9:
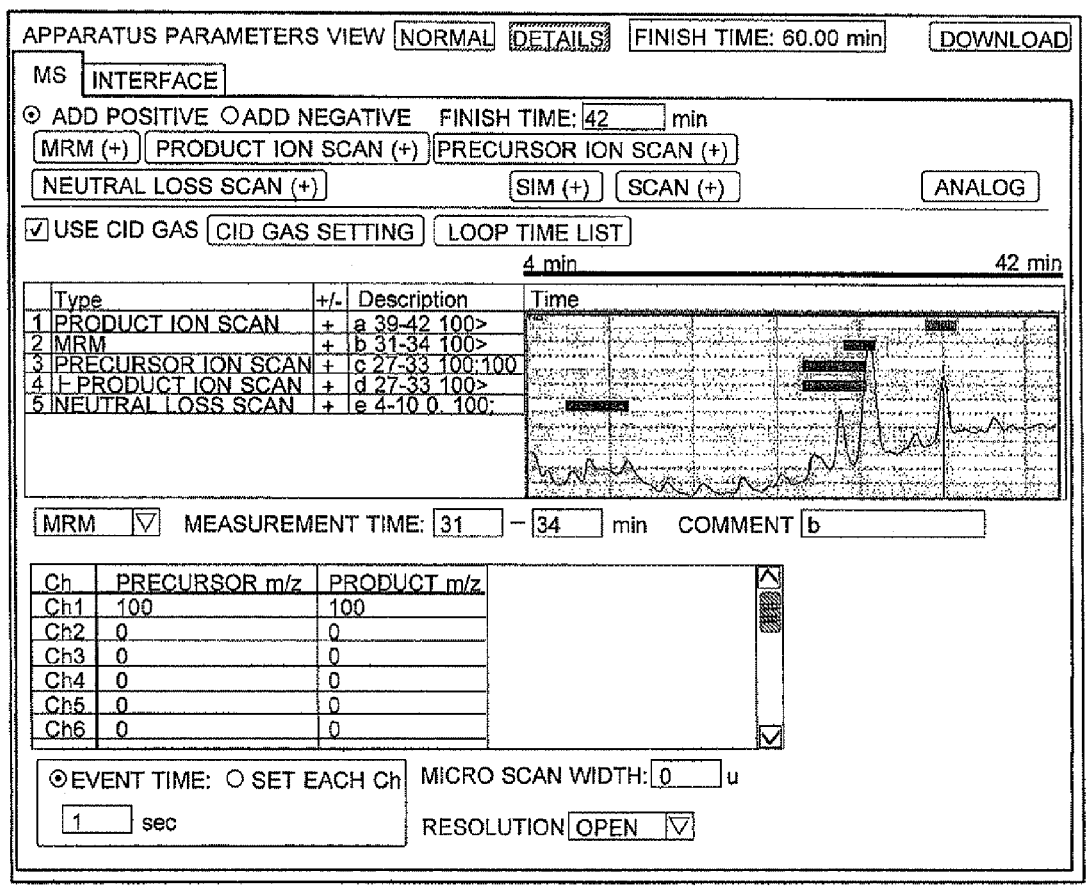
FIG. 9 shows an example of a screen of a conventional analyzing apparatus control application.

The range altering section 36 adjusts the length of a range bar in the measurement time range display area 41 in response to a relevant user operation of the input unit 16 such as a mouse. FIG. 7 shows a schematic diagram which illustrates the position change of a range bar by a drag operation. In addition to this operation, the range altering section 36 changes the position and length of a target range bar in the measurement time range display area 41 in response to such operations as range bar lengthening or shortening.

When the position or length of a range bar is changed by the range altering section 36 as just described, the measurement time reconfigurator 37 reconfigures the time range of the conditions of the measurement which corresponds to that range bar. At the same time, if the loop time computational result window 5 is shown on the monitor 14, the loop time displayer 32 recomputes the loop time and the number of events that temporally overlap each other, and reflects the latest values in the loop time computational result window 5. The loop time warning section 34 also repeats the operation as previously described.

The analyzing apparatus control system according to the present invention has been described by using an embodiment. It should be noted that the embodiment described thus far is merely an example, and it is evident that any appropriate modification, adjustment, or addition can be made within the spirit of the present invention.

For example, the loop time displayer may display the loop time or the number of measurements which temporally overlap each other immediately above or below the measurement time range display area at a position corresponding to the range bars rather than opening a loop time computational result window in a separate window.

Explanation of Numerals
1 . . . Analyzing Apparatus Control System
4 . . . Measurement Condition Setting Screen
5 . . . Loop Time Computational Result Window
10 . . . CPU
12 . . . Memory
14 . . . Monitor
16 . . . Input Unit
18 . . . IIF
20 . . . Memory Unit
21 . . . Program for Analyzing Apparatus Control Unit
22 . . . Reference Chromatogram Memory Unit
23 . . . OS
31 . . . Time Range Displayer
32 . . . Loop Time Displayer
33 . . . Chromatogram Displayer
34 . . . Loop Time Warning Section
35 . . . Designated Time Range Exhibitor
36 . . . Range Altering Section
37 . . . Measurement Time Reconfigurator
40 . . . Measurement Addition Button Area
41 . . . Measurement Time Range Display Area
42 . . . Measurement Condition Name Display Area
43 . . . Loop Time Display Button
51 . . . Mouse Pointer
A1 . . . Analyzing Apparatus

The invention claimed is:

1. An analyzing apparatus control system for controlling an analyzing apparatus so as to temporally separate a sample to be examined by a chromatograph, and repeat unit measurements in each of one or more measurement time ranges set in a total measurement time, where a unit measurement includes one or more measurements carried out under predetermined conditions, the analyzing apparatus control system comprising:
   a) a time range displayer for displaying time ranges, in each of which each of one or more measurements is carried out under predetermined conditions and displayed as a range bar; and
   b) a loop time displayer for computing a loop time, which is a summation of times of all measurements included in the unit measurement and times for operations, for each of the measurement time ranges and displaying results of computations.

2. The analyzing apparatus control system according to claim 1, wherein the loop time displayer displays a list of the results of the computations so as to show a temporal change of the loop time.

3. The analyzing apparatus control system according to claim 1, further comprising a chromatogram displayer for displaying a reference chromatogram which corresponds to the sample to be examined, wherein
   the time range displayer displays the range bars so as to temporally overlap the reference chromatogram which is displayed by the chromatogram displayer.

4. The analyzing apparatus control system according to claim 1, wherein the loop time displayer further detects a time range in which a plurality of measurements temporally overlap each other and displays a number of the overlaps together with the results of the computations.

5. The analyzing apparatus control system according to claim 1, further comprising a loop time warning unit for comparing the loop time with a predetermined value and displaying a warning if the loop time exceeds the value.

6. The analyzing apparatus control system according to claim 1, further comprising a designated time range exhibitor for displaying, in response to a designation of a time range of a loop time included in the results of the computations which are shown, the designated time range so as to overlap the range bars which are shown on the reference chromatogram.

7. The analyzing apparatus control system according to claim 6, wherein the designated time range exhibitor further changes an order of the range bars so that multiple range bars existing in the designated time range of the loop time are situated adjacently.

8. The analyzing apparatus control system according to claim 1, further comprising:
   a range altering section for changing, in response to an indication by a user, a temporal position and/or a length of a range bar shown by the time range displayer; and
   a measurement time reconfigurator for reconfigurating, in response to a change of the temporal position and/or the length of the range bar by the range altering section, wherein:
   the loop time displayer recomputes the loop time for each of the time ranges in response to the change of the temporal position and/or the length of the range bar by the range altering section.

9. A non-transitory computer readable storage media recording a program for an analyzing apparatus control system for controlling an analyzing apparatus so as to temporally separate a sample to be examined by a chromatograph, and repeat unit measurements in each of one or more measurement time ranges set in a total measurement time, where a unit measurement includes one or more measurements carried out under predetermined conditions, the program being for making a computer which executes the program function as:
   a) a time range displayer for displaying time ranges, in each of which each of the one or more measurements is carried out under predetermined conditions and displayed as a range bar; and
   b) a loop time displayer for computing a loop time, which is a summation of times of all measurements included in the unit measurement and times for operations, for each of the measurement time ranges and displaying results of computations.

* * * * *